(12) United States Patent
Suzuki et al.

(10) Patent No.: US 6,590,953 B2
(45) Date of Patent: Jul. 8, 2003

(54) X-RAY CT SCANNER

(75) Inventors: Tsutomu Suzuki, Abiko (JP); Hiroshi Takano, Kitasoma-gun (JP); Eiichi Makino, Nagareyama (JP); Takaaki Kobiki, Noda (JP); Akira Kurome, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/949,638

(22) Filed: Sep. 12, 2001

(65) Prior Publication Data

US 2002/0031201 A1 Mar. 14, 2002

(30) Foreign Application Priority Data

Sep. 12, 2000 (JP) .......................................... 2000-276306
Mar. 1, 2001 (JP) .......................................... 2001-056830
Jul. 26, 2001 (JP) .......................................... 2001-226334

(51) Int. Cl.7 .............................. H05G 1/60; H02K 1/12; H02K 1/22
(52) U.S. Cl. .......................... 378/15; 310/211; 310/254; 310/266
(58) Field of Search ............................... 378/4, 15, 197, 378/198; 310/12, 166, 266, 254, 211

(56) References Cited

U.S. PATENT DOCUMENTS 4,095,150 A * 6/1978 Senckel ........................ 310/12
4,761,602 A * 8/1988 Leibovich .................... 310/816
5,631,944 A * 5/1997 Kimura et al. .............. 378/134

* cited by examiner

Primary Examiner—Drew A. Dunn
Assistant Examiner—Allen C. Ho
(74) Attorney, Agent, or Firm—Antonelli, Terry, Stout & Kraus, LLP

(57) ABSTRACT

The rotary member carrying the X-ray radiation unfit and the X-ray detection unit and rotated around a subject is used as the rotor. The rotor is provided with a rotor core and a plurality of conductors connected to the core. The stator has at least one set of stator core and stator winding, the at least one set of stator core and stator winding being adapted to clamp the rotor and arranged at opposing positions. A three-phase AC current is supplied to the stator winding to generate a rotating magnetic field to rotate the rotor and thereby rotate the rotary member at high speed. Because the scan time can be reduced, the X-ray CT scanner can scan such moving organs as heart.

15 Claims, 8 Drawing Sheets

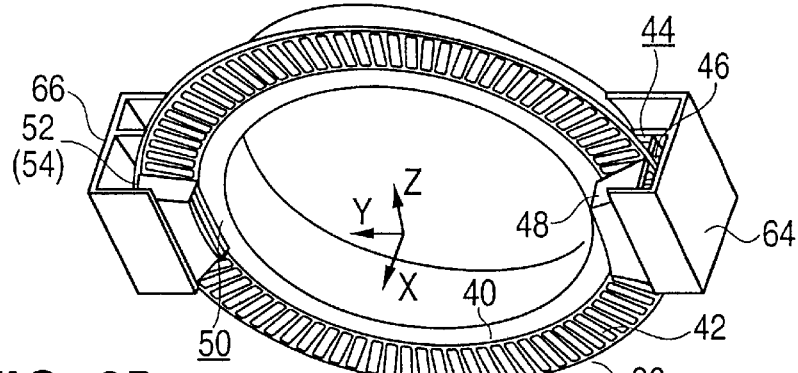
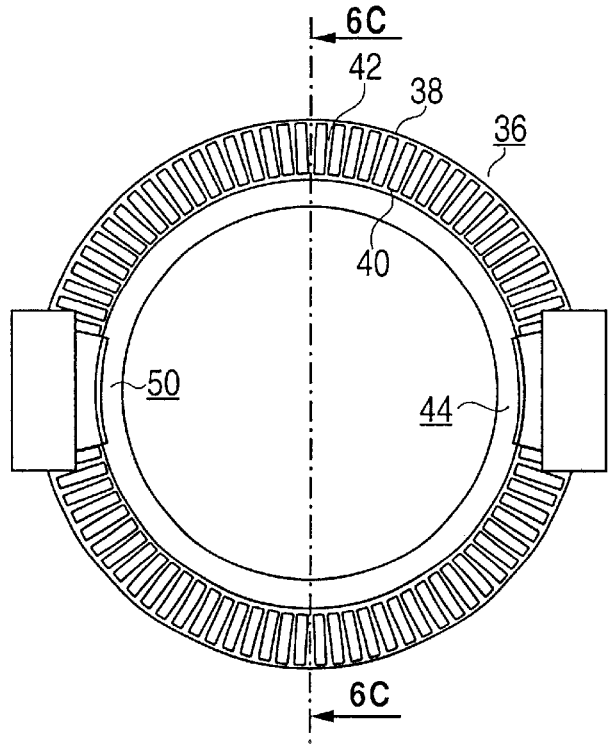
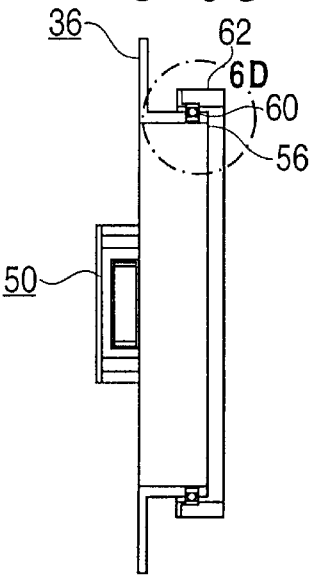
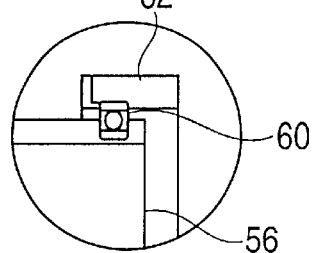

State of eddy current

State of eddy current

X-RAY CT SCANNER

BACKGROUND OF THE INVENTION

The present invention relates to an X-ray CT scanner and more particularly to an X-ray CT scanner with a scanner rotation mechanism suited for shortening a scan time by rotating a scanner at high speeds.

The X-ray CT scanner produces a cross-sectional image or tomogram of a subject by radiating a fan-shaped X-ray beam from an X-ray tube onto a subject, detecting X-rays that have penetrated the subject with an X-ray detector arranged at a position opposite the X-ray tube, and image-processing data on the detected X-rays.

The X-ray detector has a group of as many as several hundred detection elements arranged in arc, and is placed opposite the X-ray tube with the subject therebetween to form radially distributed X-ray paths in a number corresponding to that of the detection elements. The X-ray tube and the detector are rotated together around the subject through at least 180 degrees to detect X-rays that have penetrated the subject at intervals of a predetermined angle.

Thanks to advantages this X-ray CT scanner has achieved in recent years, such as capabilities of "scanning a wide range in a short period of time" and of "producing continuous data in a body axis direction and thereby generating a three-dimensional image," a spiral CT performing a helical or spiral scan has found a rapidly growing range of applications.

The spiral CT has enabled a substantial reduction in the time required to perform a three-dimensional CT imaging by continuously rotating the X-ray tube and X-ray detector around a subject while moving a table on which the subject is placed, collecting cross-sectional image data in multiple layers over a wide range and reconstructing the data into an image.

The X-ray CT scanner normally includes a plurality of units: a scanner for rotating the X-ray tube and X-ray detector around a subject to take data on the X-rays that have penetrated the subject; a subject table having a table on which the subject is placed; an image processor for processing the X-ray data collected by the scanner to generate a reconstructed image; a display device for displaying the image reconstructed by the image processor; a keyboard with which to enter various commands; and a system controller for controlling a whole system.

The scanner includes an X-ray tube for radiating X-rays against a subject; a collimator for collimating the X-rays radiated from the X-ray tube into a fan beam; a cooler for cooling the X-ray tube; a high-voltage generator for applying a high voltage to the X-ray tube; a multichannel X-ray detector for detecting X-rays that have penetrated the subject; an amplifier for amplifying a weak electric output of the X-ray detector; a rotary member supporting these devices and having a circular hole in which to position the subject at the center thereof; a frame for rotatably supporting the rotary member; a reduction gear and a motor secured to the frame to rotate the rotary member; and a belt (normally a toothed belt) for coupling the rotary member and an output shaft of the reduction gear.

In a scanner of such a construction, when the motor is started, the rotary power of the motor output shaft is reduced in speed by the reduction gear and conveyed through the belt to the rotary member, which then rotates the X-ray tube and the X-ray detector around a subject to produce X-ray projection data (this is also referred to as imaging or scanning) at intervals of a predetermined angle. The rotary member carrying the X-ray tube and the high-voltage generator, because it is capable of counter-weight mounting, can easily establish a mass balance around a rotating axis. Further, since it does not need to be accelerated to high speeds, the rotary member needs only to be rotated at an almost constant speed. Hence, the motor often employs an induction motor based on an open-loop control.

The conventional X-ray CT scanner usually uses a motor for an actuator that rotates the rotary member by reducing the rotation speed of the motor by the reduction gear and transmitting the rotation through a power transmission means such as a belt to the rotary member.

In addition to the X-ray radiation unit and the X-ray detection unit, the rotary member has a high-voltage generation unit for applying a high voltage to the X-ray radiation unit, a cooling unit for cooling the X-ray radiation unit, and an amplifier unit for amplifying a weak electric output from the X-ray detection unit. These units are rigidly fixed to the center of the rotary member from the outer circumferential side by fixing means such as screws.

In the X-ray CT scanner, the widespread use of the spiral CT has led to a significant improvement on a diagnostic technique as described above. There are also growing demands for imaging dynamically moving internal organs such as heart.

To meet these demands, the rotation speed of the X-ray tube and X-ray detector needs to be increased to shorten the scan time. That is, the rotation speed of the rotary member of the scanner must be raised. While the scan time of 1 second/rotation poses no problem for organs other than heart, the imaging of such moving organs such as heart cannot be realized with the rotation speed of 1 second/rotation but requires a higher scan speed of 0.7 to 0.5 second/rotation or even 0.3 second/rotation.

Driving the rotary member at a high rotating speed less than 0.7 second/rotation by using a conventional scanner rotary drive mechanism described above, however, causes the toothed belt to produce a whizzing sound in excess of 70 dB. Since the X-ray CT scanner is used in an inspection room in a hospital where quietness is required, noise of such a level is offensive to the ear of a subject and an operator. To solve this noise problem and still realize a high speed rotation requires the rotary member to be rotated in a direct drive (DD) mode where the rotary member itself is constructed as a rotor of the motor, rather than being rotated through the reduction gear and belt.

Two DD methods are conceivable.

As with general industrial motors, one method uses a permanent magnet to generate a rotary force in the rotary member, and the other induces a rotating magnetic field around the rotary member and uses an electromotive force induced in the rotary member. In the method using the permanent magnet, however, since the rotary member has at its central part a circular hole about 1,000 mm in diameter through which to pass a subject (a subject insertion opening), if a hollow rotor with a hole about 1,000 mm across is to be made from a permanent magnet, the rotary member increases in size and cost and becomes more difficult to manufacture.

On the other hand, in the method using an induced electromotive force, because rotating fluxes generated around the rotor pass through the hole of the rotary member, if a subject is attached with a pacemaker or an electrocardiograph, these devices are likely to be operated undesirably by the rotating fluxes threading through the hole of the rotary member, which must be avoided.

Further, in either method using a permanent magnet or an induced electromagnetic force, a large amount of electromagnetic noise may leak out and interfere with a signal of the amplifier, which amplifies the weak electric output, resulting in a possible degradation of quality of a finally obtained image. To solve such a problem of electromagnetic noise, a measure should be taken to shield the DD motor including the rotary member, which in turn makes the scanner large, hindering the fast rotation of the rotary member.

On the other hand, shortening the scan time poses another problem.

As the scan time decreases, the rotary member must be rotated at an increased speed. The substantial improvements on the diagnostic technique made possible by the widespread use of the spiral CT scanner require an increase in the number of scanning operations performed, which in turn requires the X-ray radiation unit to have a large capacity.

The large-capacity X-ray radiation unit has an increased size and mass, which naturally increases the size and mass of the cooling unit and the high-voltage generation unit.

Since centrifugal forces acting on the units of the rotary member are proportional to the square of a rotational angular speed, when the rotary member incorporating the units such as X-ray radiation unit with increased sizes and masses is rotated at high speed, it is difficult to secure a sufficient mechanical strength in the conventional construction in which the units are mounted to the rotary member with such fixing means as screws.

For improvement on this problem, JP-A-9-56710 proposes an X-ray CT scanner in which the rotary member is formed like a drum and incorporates the units therein. This construction has a drawback that heat produced by the X-ray radiation unit and the high-voltage generation unit is trapped and builds up in the drum.

Especially when the X-ray radiation unit and the high-voltage generation unit are increased in their capacity to shorten the scan time, the amount of heat produced by these units is huge and the interior of the drum in which the heat is trapped becomes very hot, degrading the performance of the units installed in the drum, making it impossible to produce a cross sectional image with high precision, or shortening the service lives of the units.

The above-described JP-A-9-56710 also describes an X-ray CT scanner in which blade members are provided in the drum to send in air as the drum rotates to dissipate heat from inside the drum. The provision of the blade members in the drum, however, raises a problem of causing whizzing noise during the drum rotation, which may deteriorate the inspection environment and make the subject uneasy.

SUMMARY OF THE INVENTION

An object of the present invention is to provide an X-ray CT scanner which can increase the scanner rotation speed to reduce the scan time and thereby enable the scanning of such moving organs as heart, by using a scanner rotating mechanism that can reduce rotating magnetic fluxes threading through an opening formed in a scanner rotary member and electro-magnetic noise and secure a sufficient mechanical strength.

To achieve the above objective, a first aspect of the present invention provides an X-ray CT scanner comprising: an X-ray radiation means for radiating X-rays against a subject; an X-ray detection means arranged at a position opposite the X-ray radiation means with respect to the subject; an opening in which to put the subject; a rotary member at least mounting the X-ray radiation means and the X-ray detection means and rotated around the subject; a rotary drive means for rotating the rotary member; and a frame for supporting the rotary member and a rotary drive means; wherein information on the X-rays that have penetrated the subject and are detected by the X-ray detection means is processed to generate a cross-sectional image of the subject; wherein the rotary drive means has a rotor and a stator, the rotary member is used as the rotor, the rotor is provided with a rotor core and a plurality of conductors connected to the rotor core, and the stator comprises at least one set of stator core and stator winding, the at least one set of stator core and stator winding being adapted to clamp the rotor and arranged at opposing positions; wherein a three-phase AC current is passed through the stator winding to generate a rotating magnetic field to rotate the rotor and therefore the rotary member.

The rotor may comprise short-circuit rings provided on an inner circumference and an outer circumference, respectively, of a rotating axis of the rotor core made from a magnetic metal and a plurality of conductors connected to ends of these short-circuit rings.

The rotor may comprise two short-circuit rings of different diameters provided on almost the same circumferential plane of the rotor core and a plurality of conductors connected to ends of these short-circuit rings.

The rotor core may be formed by laminating silicon steel plates punched with a plurality of slots, the conductors may be installed in the plurality of slots, and the ends of the conductors may be connected to the short-circuit rings.

A second aspect of the present invention provides an X-ray CT scanner comprising: an X-ray radiation means for radiating X-rays against a subject; an X-ray detection means arranged at a position opposite the X-ray radiation means with respect to the subject; an opening in which to put the subject; a rotary member mounting at least the X-ray radiation means and the X-ray detection means and rotated around the subject; a rotary drive means for rotating the rotary member; and a frame for supporting the rotary member and a rotary drive means; wherein information on the X-rays that have penetrated the subject and are detected by the X-ray detection means is processed to generate a cross-sectional image of the subject; wherein the rotary drive means has a rotor and a stator, the rotary member is used as the rotor, the rotor comprises a magnetic metal body and conductors connected to both surfaces of the magnetic metal body, and the stator comprises at least one set of stator core and stator winding, the at least one set of stator core and stator winding being adapted to clamp the rotor and arranged at opposing positions; wherein a three-phase AC current is passed through the stator winding to generate a rotating magnetic field to rotate the rotor and therefore the rotary member.

The rotor core may be formed by fixing plate conductors to both surfaces of the magnetic metal body. When a plurality of stators are provided, they may be arranged at almost equal intervals in the circumferential direction of the rotor.

With the above construction, the rotating magnetic fluxes generated by the stator arranged on the outer circumferential portion or on one surface side of the rotor and by the stator arranged on the inner circumferential portion or on the other surface side of the rotor do not leak out of the two stators and thus can be used for producing a rotation torque of the rotor. This construction does not require a large-diameter permanent magnet, which is difficult to manufacture, and therefore achieves a low-noise, high-speed rotation of the scanner by using a direct drive system, which in turn realizes a high-quality image immune from electromagnetic noise and a reduced scan time and enables the scanning of dynamically moving internal organs such as heart.

A third aspect of the present invention provides an X-ray CT scanner comprising: an X-ray tube for radiating X-rays against a subject; an X-ray detector for detecting X-rays that have penetrated the subject; a plate-like rotary member having the X-ray tube and the X-ray detector mounted thereon at opposing positions with the subject therebetween; a support means for rotatably supporting the rotary member; and a rotary drive means for rotating the rotary member about the subject; wherein a unit mounting means having an accommodating portion and a mounting member erected near the accommodating portion is provided on the rotary member at at least one location, and at least one of units is mounted to the mounting member of the unit mounting means from a center side of the rotary member.

The accommodating portion of the unit mounting means may be formed by recessing or cutting away a part of the rotary member, and the mounting member may be integrally erected from the rotary member almost perpendicular to a unit mounting surface of the rotary member on the outer circumferential side of the accommodating portion.

The mounting member of the unit mounting means may be divided into a long side portion and a short side portion, the accommodating portion may be formed by recessing or cutting away a part of the rotary member, and at a location near the accommodating portion the short side portion of the mounting member may be bent almost perpendicular to a unit mounting surface of the rotary member and the long side portion of the mounting member may be secured to an outer circumferential side end of the short side portion of the mounting member.

With this construction, since there are no components around the rotary member that hinder heat dissipation, heat is not trapped inside the rotary member, thus preventing possible performance degradations or reduced service lives of the units mounted on the rotary member. This allows a highly accurate tomogram to be generated over a long period of time. Further, since noise is not produced even at high-speed rotation of the rotary member, the inspection environment can be prevented from deteriorating or giving uneasiness to a subject.

Since the centrifugal forces acting on the units that are generated when the rotary member is rotated at high speed are carried by the rotary member through the mounting members of the unit mounting means, the X-ray CT scanner can secure a sufficient strength to withstand the centrifugal forces without having to increase the mechanical strength of each unit even when the sizes and masses of the units increase. Further, because the centrifugal forces do not act directly on the fixing means that fixes the units to the mounting members, the fixing means can be prevented from becoming loose or failing due to excess centrifugal forces and the units from coming off.

Further, since the mounting members are erected from the rotary member, the rotary member has an increased section modulus, making it possible to improve the rigidity and mechanical strength of the rotary member without having to increase the plate thickness of the rotary member. Compared with the construction in which the plate thickness of the rotary member is increased for improved rigidity and mechanical strength, this construction can minimize an increase in the mass of the rotary member and therefore reduce the moment of inertia when the rotary member is rotated at high speed. Further, because the rotary drive means for driving the rotary member does not require a large capacity, the equipment as a whole can be made small and less costly and power consumption reduced.

Further, since the accommodating portion of the unit mounting means is formed by recessing or cutting away a part of the rotary member and the mounting member is integrally erected from the rotary member almost perpendicular to the unit mounting surface of the rotary member on the outer circumferential side of the accommodating portion, the rotary member can be formed highly accurately by means of casting and at the same time can reliably support even the units of large masses.

Further, the mounting member of the unit mounting means is divided into a long side portion and a short side portion; the accommodating portion is formed by recessing or cutting away a part of the rotary member; and near the accommodating portion, the short side portion of the mounting member is bent almost perpendicular to the unit mounting surface of the rotary member and the long side portion of the mounting member is secured to the outer circumferential side end of the short side portion of the mounting member. This construction can reduce the weight of the rotary member without lowering the rigidity and mechanical strength of the rotary member. Because simply replacing the long side portion of the mounting member can easily deal with the specification changes of the unit, the unit specification changes can be accomplished much more economically than when the entire rotary member is replaced according to the specification changes.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

FIG. 6A is a perspective view showing a rotary drive mechanism of a scanner making up the X-ray CT scanner as a second embodiment of the present invention.

FIG. 6B is a front view showing the rotary drive mechanism of the scanner making up the X-ray CT scanner as the second embodiment of the present invention.

FIG. 6C is a cross-sectional view taken along the line 60 of FIG. 6B.

FIG. 6D is an enlarged view of a part of FIG. 6C enclosed in a circle.

DETAILED DESCRIPTION OF THE EMBODIMENTS

Now, embodiments of the present invention will be explained in detail by referring to FIG. 1 through FIG. 10.

(1) Embodiments of Scanner

Figure 1:
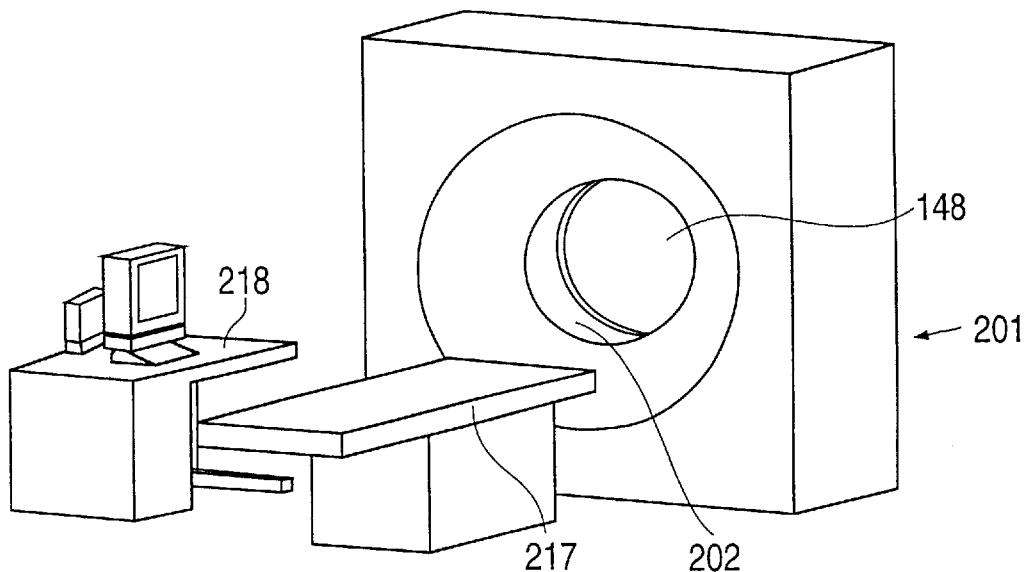
FIG. 1 is an overall perspective view showing an X-ray CT scanner as one embodiment of the present invention.
Figure 2A:
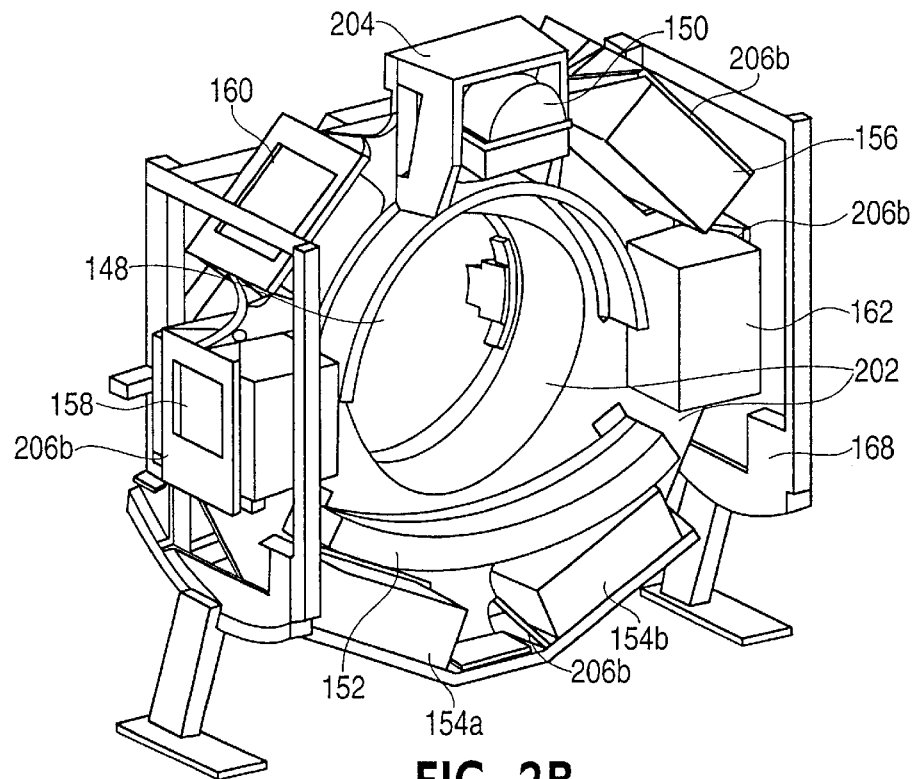
FIG. 2A is a front perspective view showing an inner construction of a scanner making up the X-ray CT scanner as a fourth embodiment of the present invention.
Figure 2B:
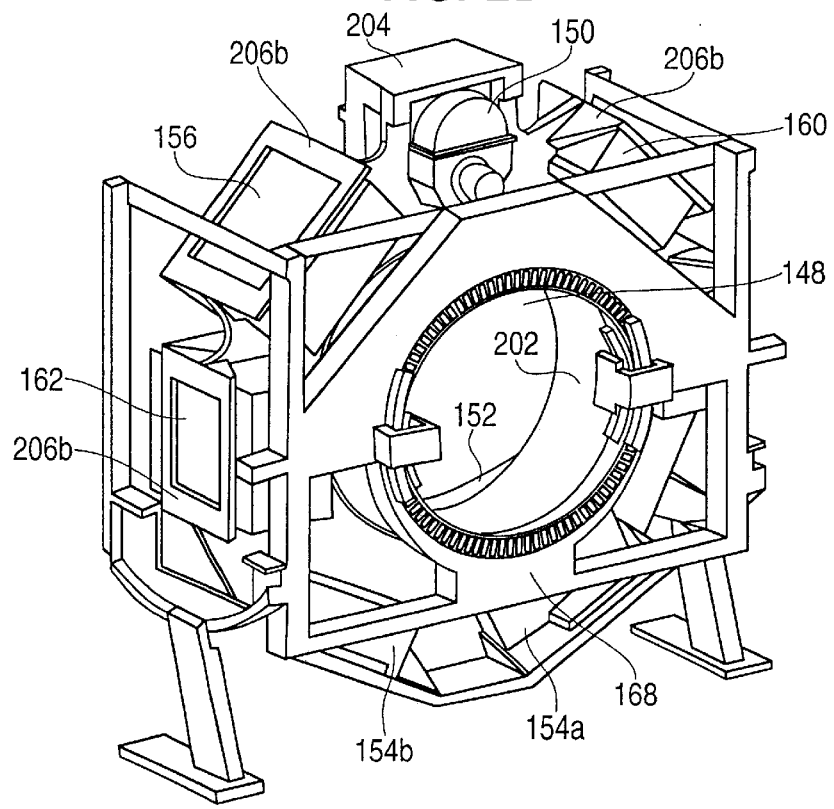
FIG. 2B is a rear perspective view showing an inner construction of the scanner making up the X-ray CT scanner as the fourth embodiment of the present invention.

FIG. 1 is an overall perspective view of an X-ray CT scanner capable of performing a spiral scan, and FIG. 2A and FIG. 2B show inner constructions of the scanner.

The X-ray CT scanner shown in FIG. 1 comprises a scanner 201, a subject bed 217 on which a subject (not shown) is laid, and an operation desk 218 for operating the X-ray CT scanner.

A subject lying on the subject bed 217 of FIG. 1 is passed through an opening 148 with a body axis of the subject aligned with an X-axis direction. Designated 150 is an X-ray tube for radiating X-rays. X-rays are radiated against the subject and those X-rays that have penetrated the subject are detected by an X-ray detector 152 which converts them into an electric signal. The X-ray detector is a multichannel detector and the weak electric signal produced by the detector is amplified by amplifiers 154a, 154b.

As an X-ray high-voltage generator for generating a DC high voltage of several tens of kV or higher to be applied to the X-ray tube 150, an inverter type X-ray high-voltage generator is used which rectifies a utility power to a DC power, transforms the rectified DC voltage into a high-frequency AC voltage by an inverter circuit, raises the high-frequency AC voltage by a high-voltage transformer, and transforms the raised AC voltage to a DC voltage again by a rectifier circuit, thus generating a high DC voltage. This construction makes the X-ray high-voltage generator small enough to be installed in a scanner rotary portion.

This inverter type X-ray high-voltage generator comprises an X-ray control unit 158 and a high-voltage generation unit 160. The X-ray control unit 158 has an inverter circuit for rectifying a utility power into a DC power and transforming the rectified DC voltage to a high-frequency AC voltage, and a control circuit for the inverter circuit. The high-voltage generation unit 160 has a high-voltage transformer and a high voltage rectifier circuit for raising an output voltage of the inverter circuit and rectifying the raised voltage. These are mounted in the scanner rotary portion as shown in FIG. 2A and FIG. 2B.

The inverter type X-ray high voltage generator may be installed either in the scanner rotary portion or in a stationary portion. FIGS. 2A and 2B show an example case where the voltage generator is installed in the scanner rotary portion.

Denoted 156 is a cooler which circulates oil through the X-ray tube and cools the oil by air to cool the X-ray tube. A controller 162 controls the cooler 156 and other units not shown.

Designated 202 is a rotary member that mounts the X-ray tube 150, X-ray detector 152, amplifiers 154a, 154b, X-ray control unit 158, high-voltage generation unit 160, controller 162 and others. The rotary member 202 is supported on a frame 168 by bearings not shown so that it is rotatable about the X-axis. The rotary member 202 has a rotor 2 (FIG. 3A) and the frame 168 has stators 10, 16 (FIG. 3A) which are divided in two and separated in a circumferential direction to generate two rotating magnetic fields. The rotor 2 may be formed into a disk shape. A detailed construction of the rotary member 202 will be described in a fourth embodiment.

The construction described above can reduce the thickness in the X-axis direction of the scanner, enhancing a space efficiency of the installation environment and reducing its oppressive impression on the subject. This construction can also realize an X-ray CT scanner that performs a high-speed and yet quiet scan and has almost no fluxes threading through the opening. Because no fluxes pass through the interior of the opening 148, scanning a subject wearing an electrocardiograph or pacemaker does not cause false operations of these devices. Hence, safe scanning operations can be made.

(2) Scanner Rotary Mechanism Based on Direct Drive System (First Embodiment)

Figure 3A:
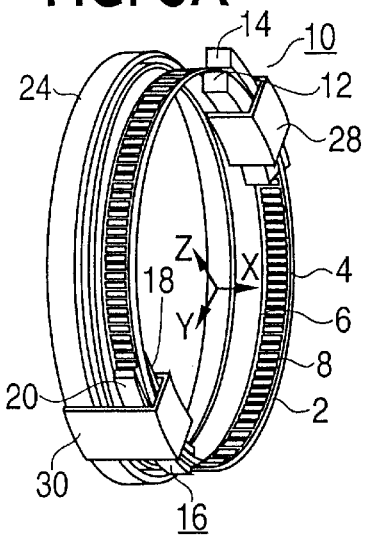
FIG. 3A is a perspective view showing a rotary drive mechanism of a scanner making up the X-ray CT scanner as a first embodiment of the present invention.
Figure 3B:
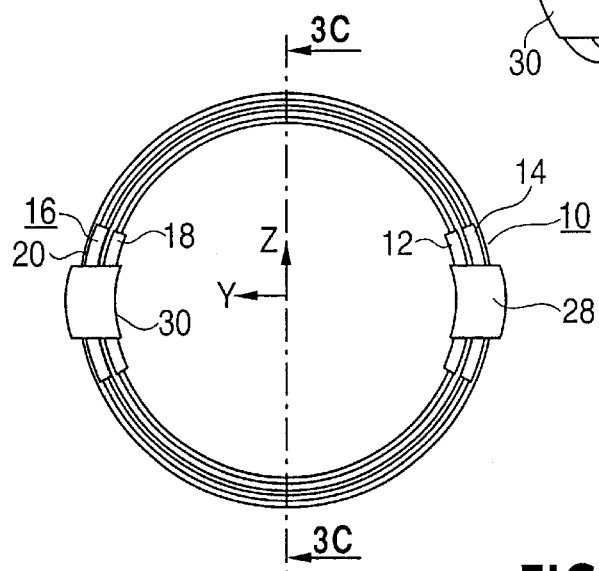
FIG. 3B is a front view showing the rotary drive mechanism of the scanner making up the X-ray CT scanner as the first embodiment of the present invention.

FIGS. 3A to 3D show a first embodiment of a direct drive scanner rotary mechanism in the X-ray CT scanner of this invention. FIG. 3A represents a perspective view, FIG. 3B a front view and FIG. 3C a cross section taken along the line 3C of FIG. 3B. The rotary member mounting the X-ray tube, the X-ray detector and others is used as the rotor 2 of the direct drive motor (DD motor). The rotor 2 comprises a rotor core (not shown) that is made up of silicon steel plates punched with slots and laminated together, two short-circuit rings 4, 6 arranged in a rotating axis (X axis) direction of the rotor 2, and a plurality of conductors 8 connected to the short-circuit rings 4, 6.

An electric material of the short-circuit rings 4, 6 and the conductors 8 uses copper or aluminum as with the conventional induction motors. The conductors 8 are installed in the slots and connected to the short-circuit rings 4, 6 so that the rotating magnetic field generated by the stator described later induces a voltage in the conductors 8, which in turn causes a current to flow through the conductors 8, producing a torque in the rotor 2 and thereby rotating it.

To reduce noise caused by harmonic components of the torque produced by the current flowing through the conductors 8, it is preferred that the conductors 8 be arranged at a slight angle to the X-axis.

The stator is divided into two sets 10, 16 which are separated in the circumferential direction of the rotor 2 and arranged along the rotor 2 at opposing positions. These stators 10, 16 are wound with stator windings described later that are supplied a multiphase AC power to generate rotating magnetic fields.

While in FIGS. 3A to 3D, we have described an example case where two stators 10, 16 and two stator windings are used to generate the rotating magnetic fields, the present invention is not limited to this number of divisions and three or more of them may be provided. Or they may be extended over an entire circumference of the rotor 2 without being divided. When they are divided, however, the stators should preferably be of almost equal size and arranged at equal intervals to avoid possible speed variations of the rotor 2 to ensure its smooth rotation.

The shapes of and the positional relation between the stators 10, 16 and the rotor 2 will be detailed later. The stators 10, 16 each comprise an outer circumferential stator 14, 20 and an inner circumferential stator 12, 18 and clamp the rotor 2 therebetween. Denoted 22 is a ring member attached to the rotor 2 which is rotatably supported on a housing 24 through a large-diameter bearing 26.

The bearing 26 may be a plurality of small-diameter bearings arranged along the circumference, rather than a single large-diameter bearing.

The housing 24 securely holds the stators 10, 16 through fixing members 28, 30.

Figure 3C:
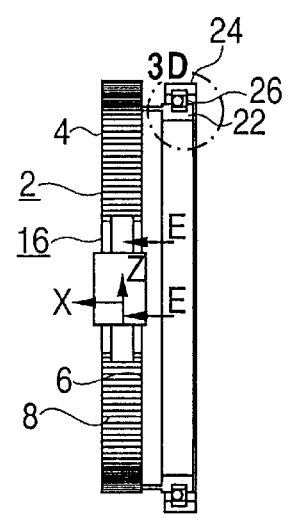
FIG. 3C is a cross-sectional view taken along the line 30 of FIG. 3B.
Figure 3D:
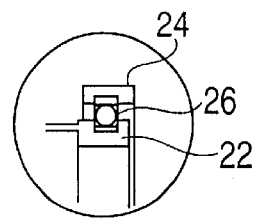
FIG. 3D is an enlarged view of a part of FIG. 3C enclosed in a circle A.
Figure 4:
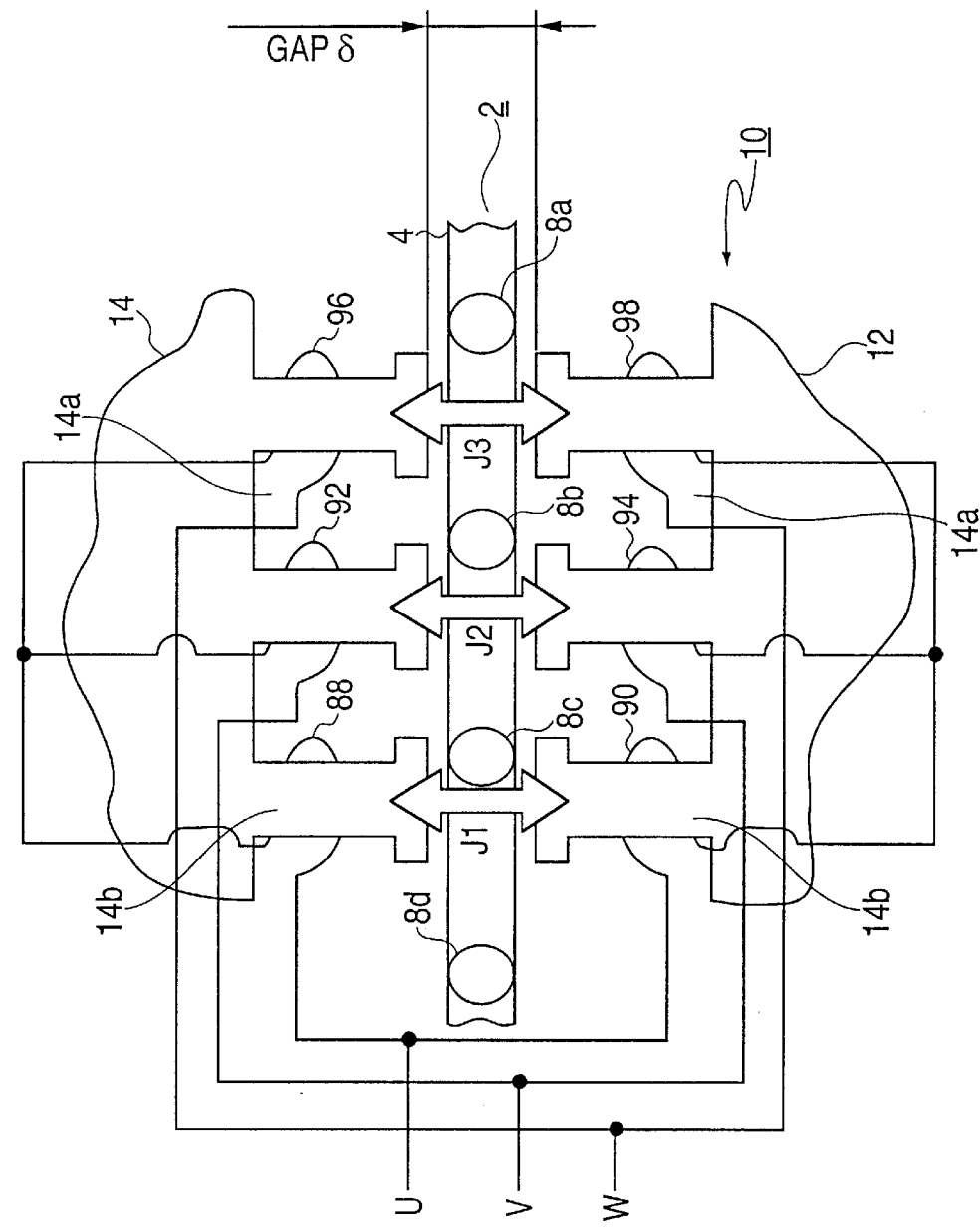
FIG. 4 is an explanatory diagram showing a stator, a stator winding and a rotor provided in the rotary drive mechanism of the scanner making up the X-ray CT scanner as the first embodiment of the present invention.

To explain the shapes and positions of the stators 10, 16, their stator windings and the rotor 2 of the first embodiment shown in FIG. 3 as well as their relations with magnetic fluxes, FIG. 4 shows an example case of the stator 10 in an E—E cross section of FIG. 3C.

In FIG. 4, the outer circumferential stator 14 and the inner circumferential stator 12 are formed with slots 14a roughly shown in FIG. 4. Raised portions 14b between the slots 14a are wound with windings 88, 90, 92, 94, 96, 98. The windings 88, 90 are located at opposing positions on both sides of the rotor 2 made up of the conductors 8a, 8b, 8c, 8d; the windings 92, 94 are located at opposing positions on both sides of the rotor 2 made up of the conductors 8a, 8b, 8c, 8d; and the windings 96, 98 are located at opposing positions on both sides of the rotor 2 made up of the conductors 8a, 8b, 8c, 8d.

In this example, because a three-phase power with a U, V, W phase difference of 120 degrees is supplied to the inner circumferential stator 12 and the outer circumferential stator 14, three sets of opposing windings are provided. The number of phases is not limited to three. The directions of windings are such that when currents of the same phase are supplied to the opposing windings, the magnetic fluxes are generated in the same direction.

It is noted that this invention places no limitations on the number of turns of each winding or the way they are wound and that the only requirement is to generate a rotating magnetic field. Hence, a method similar to that employed in the conventional induction motor can be used.

That is, although the example of FIG. 4 uses only one turn of each winding for simplicity, an appropriate number of turns may be selected to increase the flux density. As for the method of winding, a plurality of adjoining raised portions may be combined and the adjoining phases overlappingly wound. Any other methods may also be used.

Further, no limitations are placed on the number of poles. Two or more of what is shown in FIG. 4 may be arranged close together to provide two, four or a greater number of poles. The revolution speed of the rotor is determined by the number of poles and the frequency of the three-phase AC voltage fed to the stator windings. These may be set to optimum values based on the scan time of the X-ray CT scanner. To prevent magnetic fluxes from leaking into paths other than between the inner circumferential stator 12 and the outer circumferential stator 14 (i.e., prevent fluxes from threading through other than the paths indicated by arrows J1, J2 and J3) and thereby enhance magnetic coupling and efficiency, the slots 14a where the stator windings are installed are shaped as shown in FIG. 4. The slots are not limited to this geometry. Because a gap $\delta$ plays an important role in further enhancing the magnetic coupling, the slots should preferably be shaped to minimize this gap as practically as possible.

Although the rotary driving of the DD type scanner described above may be achieved by a utility power supply, an inverter circuit capable of speed control is preferably used because it enables arbitrary setting of a scanner revolution speed, because it can smoothly increase the revolution speed from the start up to the target speed that corresponds to the required scan time and because, after the target speed is reached, it can keep the revolution speed constant.

Figure 5:
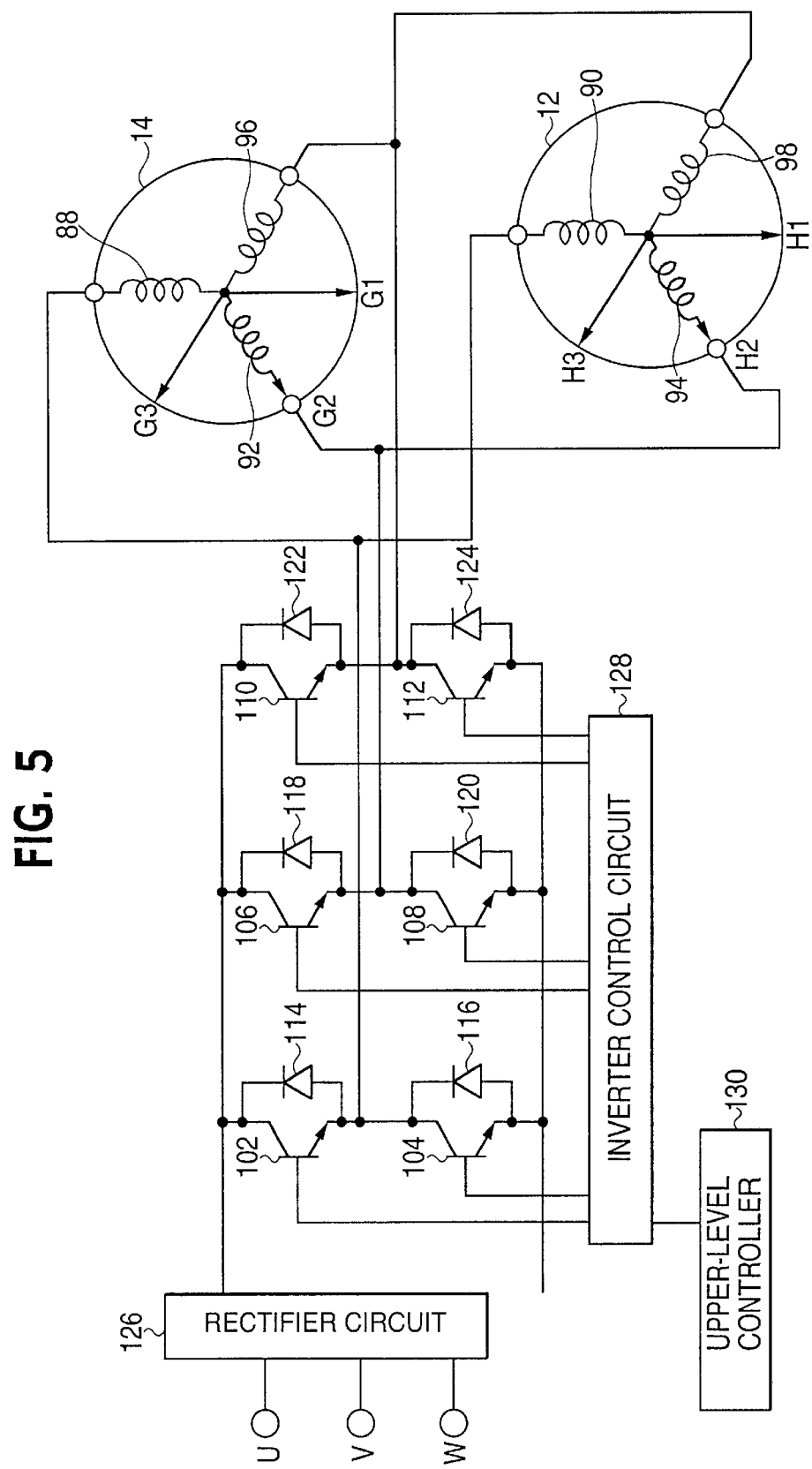
FIG. 5 is a circuit diagram showing a rotary speed control circuit of the scanner making up the X-ray CT scanner as the first embodiment of the present invention.

FIG. 5 shows a circuit using an inverter circuit to generate a three-phase AC voltage and supply this voltage to the stator windings. The inverter circuit of FIG. 5 transforms a utility three-phase AC voltage U, V, W into a DC voltage by a three-phase full-wave rectifier circuit 126 and then transforms the DC voltage into a three-phase AC voltage of a desired frequency by a known inverter circuit, which comprises six switching elements 102, 104, 106, 108, 110, 112 and diodes 114, 116, 118, 120, 122, 124 connected in anti-parallel to the switching elements. The three-phase AC voltage thus obtained is then supplied to the stator windings of the DD motor of the first embodiment shown in FIG. 3.

Insulated gate bipolar transistors (abbreviated IGBTs) are suited for the switching elements 102, 104, 106, 108, 110, 112 in the inverter circuit but other switching elements may be used. To supply output voltages u, v, w of the inverter circuit to the stator windings 90, 94, 98 of the inner circumferential stator 12 and to the stator windings 88, 92, 96 of the outer circumferential stator 14, the voltage of the u-phase terminal (connecting point between the switching element 102 and the switching element 104) of the inverter circuit is connected to the opposing stator windings 88, 90, the voltage of the v-phase terminal (connecting point between the switching element 106 and the switching element 108) is connected to the opposing stator windings 90 and 94, and the voltage of the w-phase terminal (connecting point between the switching element 110 and the switching element 112) is connected to the opposing stator windings 96 and 98.

Denoted 128 is an inverter control circuit which generates a switching signal to control the conduction/non-conduction of the IGBTs 102, 104, 106, 108, 110, 112. The inverter control circuit 128 is controlled by an upper-level controller 130 to keep the switching frequencies of the IGBTs 102, 104, 106, 108, 110, 112 at set frequencies.

Although the output voltage of the inverter circuit in this embodiment is supplied to the outer circumferential stator 14 and the inner circumferential stator 12 of the stator 10, it may also be supplied to an outer circumferential stator 20 and an inner circumferential stator 18 of the stator 16. It is also possible to form separate inverter circuits and have them individually supply their voltages to the corresponding stator windings. In this case, the output voltages of the two inverter circuits must be matched in phase. Further, as described with reference to FIG. 3, it is also possible to increase the number of divisions of the stator and still connect the divided stators to the inverter circuit in the similar manner to drive the DD motor.

Next, the operation of the scanner rotary drive mechanism in the first embodiment will be explained.

In FIG. 5, when the upper-level controller 130 issues a scan time and a scan start command to the inverter control circuit 128, the inverter control circuit 128 generates for an inverter circuit switching frequency commands corresponding to the scan time at 120-degree intervals, amplifies the generated commands and sends them to the gates of the IGBTs 102–112, or switching elements, to switch these IGBTs.

The inverter circuit thus driven now outputs a three-phase AC voltage corresponding to the switching frequency command and feeds the AC voltage to the stator windings of the outer circumferential stator 14 and the stator windings of the inner circumferential stator 12 to generate rotating magnetic fields that rotate in directions as indicated by arrow vectors G1→G2→G3, H1→H2→H3.

From FIG. 5 it is seen that, because the windings are connected so that the generated fluxes G1 and H1 have the same directions, G2 and H2 have the same directions and G3 and H3 have the same directions, the maximum flux linking with the conductors of the rotor 2 rotates in the direction of J1→J2→J3→J1 and this rotating flux induces an electromotive force in the rotor conductors 8a, 8b, 8c, 8d, which causes a current to flow in the conductors to generate a torque that rotates the rotor 2.

At this time, since the rotation of the rotor 2 lags the rotating field, a difference arises between the rotating speed of the rotating field and the speed of the rotor 2, as in the general induction motors. This is a slip.

While the above description concerns the stator 10, the same can be said of the stator 16, too.

When we look at the flux generated in this way, it is seen that the fluxes contributing to the rotation of the rotor 2 are generated only between the outer circumferential stator 14 and the inner circumferential stator 12 and between the outer circumferential stator 20 and the inner circumferential stator 18 and there is no flux threading through the interior of the opening formed at the central part of the rotor 2. Furthermore, since the stator 10 that generates the rotating fluxes exists at only a part in the circumferential direction, no flux is generated except near the stator 10. Moreover, because no permanent magnet is used, the level of electromagnetic noise is small. It is therefore possible to provide a DD motor type scanner rotary drive mechanism which is small in size, low-cost and easy to manufacture.

(Second Embodiment)

FIGS. 6A to 6D show a second embodiment of the direct-drive type scanner rotary drive mechanism in the X-ray CT scanner of this invention. FIG. 6A is a perspective view, FIG. 6B a front view, and FIG. 6C a 6C cross section of FIG. 6B. What differs from the embodiment shown in FIG. 3 is mainly the shape of a rotor 36. The rotor 36 comprises a rotor core (not shown) that is made up of silicon steel plates punched with slots and laminated together, two short-circuit rings 38, 40 arranged in virtually the same circumferential plane and having different diameters, and a plurality of conductors 42 connected to the short-circuit rings 38, 40. The conductors 42 should preferably be arranged slightly at an angle to the radial direction of the rotor 36 in order to reduce noise caused by harmonic components of the torque generated by the current flowing through the conductors 42. Further, electric materials of the short-circuit rings 38, 40 and the conductors 42 use copper or aluminum as in the conventional induction motors. The conductors 42 are installed and fixed in the individual slots and are connected to the short-circuit rings 38, 40.

The stator is divided into two sets 44, 50 which are separated in the circumferential direction of the rotor 36 and arranged along the rotor 36 at opposing positions. These stators 44, 50 are wound with stator windings, not shown, that are supplied a multiphase AC power to generate rotating magnetic fields.

While in the second embodiment shown in FIGS. 6A to 6D, we have described an example case where two stators 44, 50 and two stator windings are used to generate the rotating magnetic fields, the present invention is not limited to this number of divisions and three or more of them may be provided. Or they may be extended over an entire circumference of the rotor 36 without being divided. When they are divided, however, the stators 44, 50 should preferably be of almost equal size and arranged at equal intervals to avoid possible speed variations of the rotor 36 to ensure its smooth rotation.

The stator 44 comprises a stator 48 on one side and a stator 46 on the other side, and the other stator 50 comprises a stator 52 on one side and a stator 54 on the other side (back side of the first stator 52). These combined stators hold the rotor 36 therebetween.

Denoted 56 is a ring member attached to the rotor 36 which is rotatably supported on a housing 62 through a large-diameter bearing 60.

The bearing 60 may be a plurality of small diameter bearings arranged along the circumference, rather than a single large-diameter bearing. The housing 62 fixes the stators 44, 50 with fixing member 64, 66.

The shapes of the stators 44, 50, stator windings and rotor conductors, the arrangements of these conductors, and the rotation principle and operation of the rotor 36 using these are the same as those of the first embodiment although their reference numbers differ. Further, the drive circuit for rotating the rotor can use the circuit of FIG. 3 as is and thus their explanations are omitted here.

(Third Embodiment)

Figure 7A:
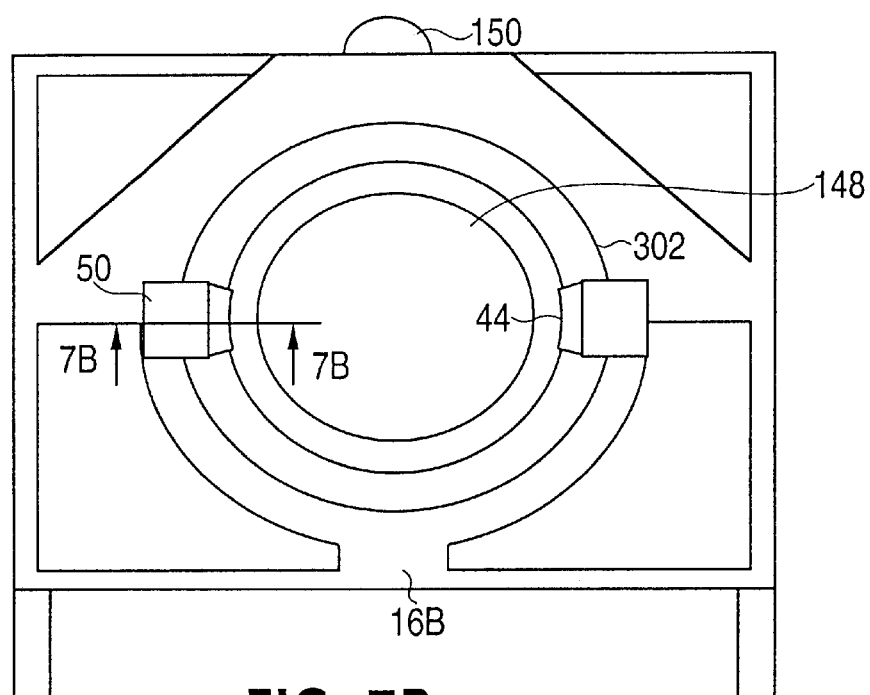
FIG. 7A is a front view showing a scanner making up the X-ray CT scanner as a third embodiment of the present invention.
Figure 7B:
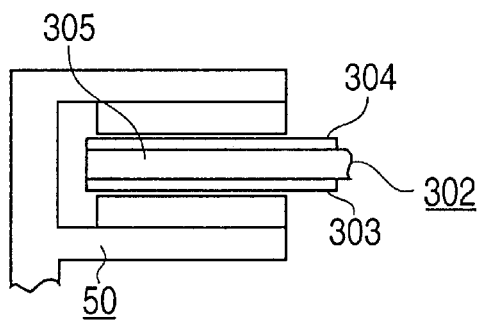
FIG. 7B is a cross-sectional view taken along the line 7B of FIG. 7A.
Figure 7C:
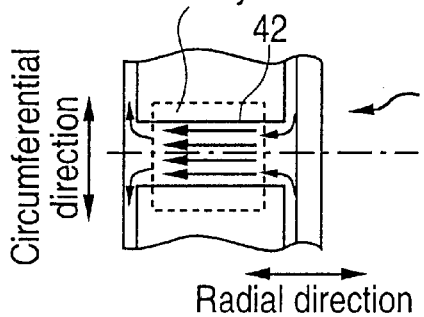
FIG. 7C is an explanatory diagram showing how an eddy current is generated.
Figure 7D:
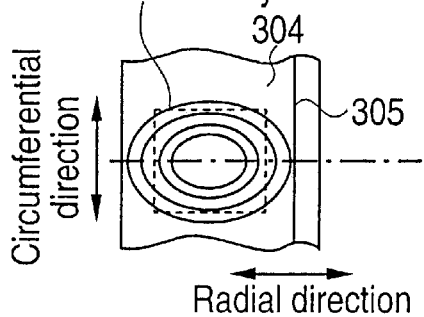
FIG. 7D is an explanatory diagram showing how an eddy current is generated.

FIGS. 7A to 7D show a third embodiment of the direct drive type rotary drive mechanism in the X-ray CT scanner of this invention. FIG. 7A is a front view of the scanner in the X-ray CT scanner, FIG. 7B is an enlarged cross section taken along the line 7B of FIG. 7A, and FIG. 7C and FIG. 7D are explanatory diagrams showing the actions of the mechanism.

While in the previous first and second embodiments, the rotor 2, 36 has a plurality of conductors 8, 42 arranged in the circumferential direction, a rotor 302 of the third embodiment comprises an annular magnetic metal body 305 and flat plate conductors 303, 304 each made of one integral plate which are secured one to each side of the magnetic metal body 305.

Further, although the laminated silicon metal plates used in the rotor core in the first and second embodiments are most advantageous in terms of magnetic permeability, they have poor machinability and may raise the manufacturing cost. The third embodiment, therefore, uses an inexpensive general use steel plate in the rotor core and forms the magnetic metal body 305 through such joining methods as explosion pressing, diffusion joining and soldering. In the case of soldering, a metal consisting mainly of gold, silver and nickel should preferably be used as a solder.

The stator is divided into two sets 44, 50 that are separated in the circumferential direction of the rotor 302 and arranged along the rotor 302 at opposing positions. These stators 44, 50 are wound with stator windings, not shown, that are supplied a multiphase AC power to generate rotating magnetic fields.

Other constructions are similar to those of the first and second embodiments and thus their explanations are omitted. When a plurality of stators 44, 50 are provided, they are preferably be arranged at equal intervals in the circumferential direction.

The operation of the scanner rotary drive mechanism of the third embodiment constructed as described above will be explained. When the rotor 2, 36 is provided with a plurality of conductors 8, 42 arranged in the circumferential direction as in the first and second embodiments, the eddy current produced in the conductors 8, 42 flows in only the radial direction of the rotor 2, 36 as shown in FIG. 7C. When the conductors 303, 304 are each formed in a single plate as in the third embodiment, the eddy current produced in the conductors 303, 304 flows in the circumferential direction in the magnetic field as shown in FIG. 7D. Hence, a force is generated not only in the radial direction of the rotor 2, 36 but also in the circumferential direction and thus the efficiency slightly deteriorates but to a degree not detrimental to the rotation of the rotor 2, 36.

(3) Construction of Rotary Member Making Up Scanner Rotary Drive Mechanism (Fourth Embodiment)

Figure 10:
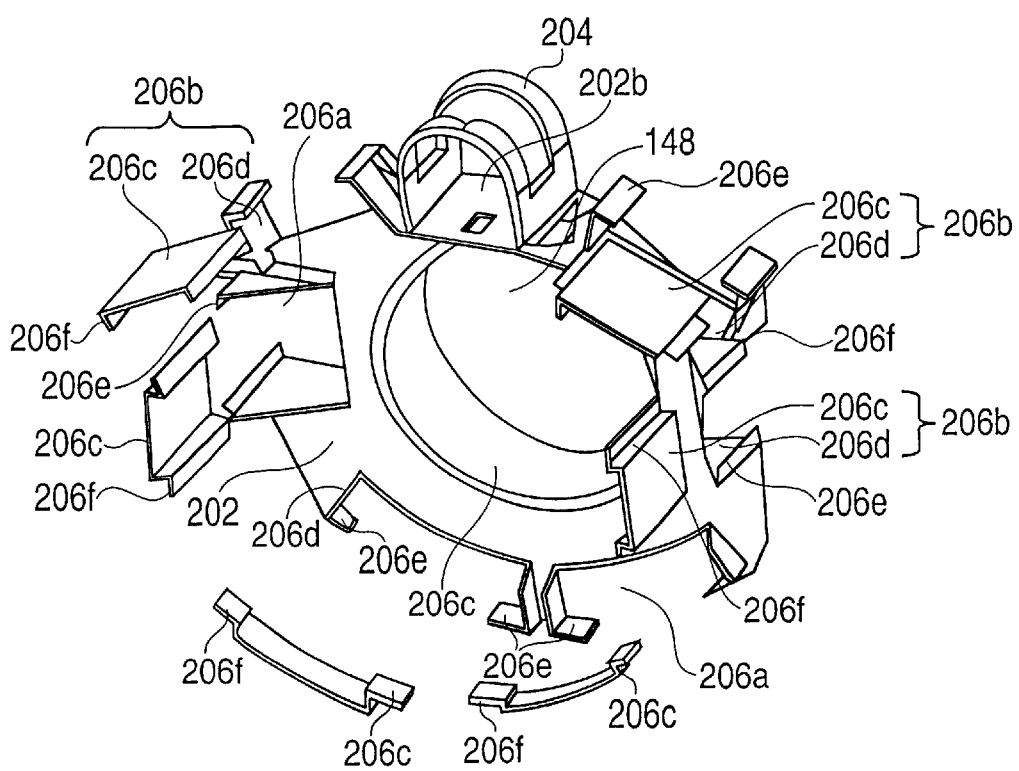
FIG. 10 is an exploded perspective view showing the variation of the rotary member provided in the scanner making up the X-ray CT scanner as the fourth embodiment of the present invention.
Figure 8:
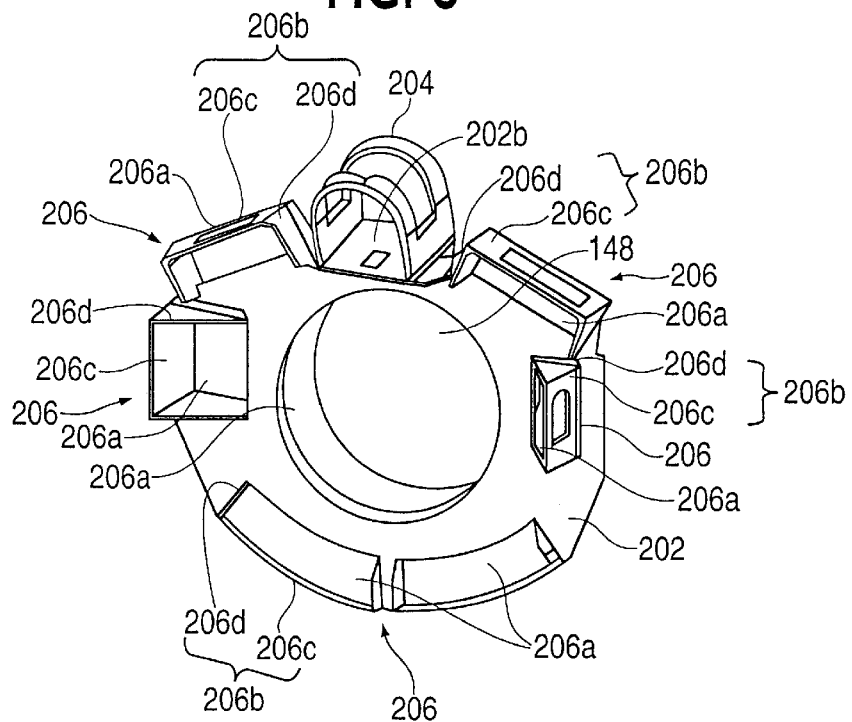
FIG. 8 is a perspective view showing a rotary member provided in a scanner making up the X-ray CT scanner as the fourth embodiment of the present invention.
Figure 9:
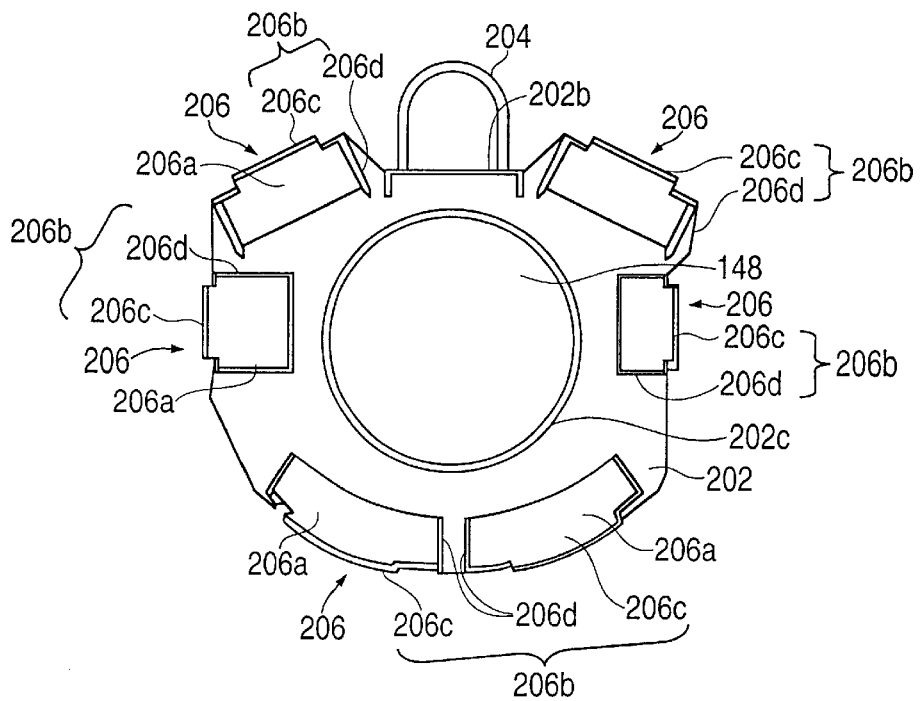
FIG. 9 is a front view showing a variation of the rotary member provided in the scanner making up the X-ray CT scanner as the fourth embodiment of the present invention.

FIG. 8 is an overall perspective view of a rotary member 202 making up the scanner rotary drive mechanism, FIG. 9 is a front view of a variation of the rotary member 202, and FIG. 10 is an exploded perspective view of a variation of the rotary member 202.

The rotary member 202 integrally formed as by casting is shaped like a plate with a circular opening 148 at the central part thereof, as shown in FIG. 8. A cylindrical portion 202c formed around the opening 148 is rotatably supported on the support frame 168 through a bearing means not shown. The rotary member 202 also has a mount 202b on the outer circumference thereof, on which to mount the X-ray tube 150.

On the mount 202b the X-ray tube 150 is mounted by an almost U-shaped mounting member 204, with an X-ray radiation portion directed to the center of the opening 148.

At a position on the rotary member 202 opposite the X-ray tube 150 with respect to the opening 148 the X-ray detector 152 for detecting X-rays radiated from the X-ray tube 150 is mounted. On the rotary member 202 are mounted a plurality of unit mounting means 206 spaced from each other in the circumferential direction.

A pair of unit mounting means 206 arranged on both sides of the X-ray tube 150 each comprise an accommodating portion 206a and a mounting member 206b. The accommodating portion 206a is formed by recessing a part of the rotary member 202 in the plate thickness direction or by cutting away a part of the rotary member 202 in a rectangular shape. The mounting member 206b is erected along three sides of the accommodating portion 206a.

The mounting member 206b, as shown in FIG. 8, is virtually U-shaped and is erected integrally from the rotary member 202 in a direction perpendicular to the mounting surface of the rotary member 202 in such a way that the long side portion 206c is on the outer circumferential side of the rotary member 202.

In one of the paired unit mounting means 206 is installed the high-voltage generation unit 160 that applies a high voltage to the X-ray tube 150. In the other unit mounting means 206 the cooler 156 for cooling the X-ray tube 150 is mounted.

The high-voltage generation unit 160 and the cooler 156 are mounted to the long side portions 206c of the mounting members 206b from the inside (from the opening 148 side) so that they are in intimate contact with the long side portions 206c. They are secured to the long side portions 206c by fixing means such as screws inserted from the outside (outer circumferential side of the rotary member 202).

Another pair of unit mounting means 206 arranged at positions opposite the X-ray tube 150 with respect to the opening 148 also have, as in the previous unit mounting means 206, an accommodating portion 206a, which is formed by recessing a part of the rotary member 202 in the plate thickness direction or by cutting away a part of the rotary member 202 in a rectangular shape, and a mounting member 206b, which is erected along three sides of the accommodating portion 206a. The virtually U-shaped mounting member 206b is erected integrally from the rotary member 202 in such a way that the long side portion 206c is on the outer circumferential side of the rotary member 202.

Another pair of unit mounting means 206 are arranged on the rotary member 202 at opposing positions with the opening 148 in between. In one of this pair of unit mounting means 206 is installed the X-ray control unit 158 and in the other unit mounting means 206 is mounted the controller 162. These X-ray control unit 158 and the controller 162 are also mounted to the long side portions 206c of the mounting members 206b from inside so that they are in intimate contact with the long side portions 206c. They are rigidly secured to the mounting members 206b by fixing means such as screws inserted from outside the mounting members 206b.

In the paired unit mounting means 206 arranged at a position opposing the X-ray tube 150 with respect to the opening 148 the amplifiers 154a, 154b are installed.

These amplifiers 154a, 154b are also mounted to the long side portion 206c of the mounting member 206b from inside so that they are in intimate contact with the long side portion 206c. They are secured to the long side portion 206c by fixing means such as screws inserted from outside the mounting member 206b.

Next, the operation of the scanner rotary drive mechanism of the fourth embodiment constructed as described above will be described.

The process of generating a tomogram by performing a spiral scan on a subject involves laying the subject on the subject bed 217 that is arranged to pass horizontally through the opening 148 of the rotary member 202, rotating the rotary member 202 at high speed by the DD motor while passing the subject through the opening, and at the same time radiating X-rays from the X-ray tube 150 against the subject.

The X-rays radiated onto the subject penetrate the subject and are detected by the X-ray detector 152 to collect data. The data thus collected is sent to an image calculation means where it is processed to produce a tomogram, which is displayed on a monitor or recorded on a recording medium such as a film.

The spiral CT scanner rotates the rotary member 202 at high speed by the DD motor to shorten the scan time.

The X-ray tube 150, the high-voltage generation unit 160, the cooler 156 and others mounted on the rotary member 202 with increased sizes and masses, when the rotary member 202 is rotated at high speed, are acted upon by centrifugal forces that are proportional to the square of a rotational angular speed. In the fourth embodiment, however, the rotary member 202 is provided with the unit mounting means 206, each of which has the accommodating portion 206a formed in the rotary member 202 and the mounting member 206b erected around the accommodating portion 206a. Because these units are installed inside the mounting members 206b situated on the outer circumferential portions of the rotary member 202, the centrifugal forces acting on the units when the rotary member 202 is rotated at high speed are carried by the rotary member 202 through the mounting members 206b. Thus, even when the units have large sizes and masses, it is possible to secure a sufficient strength to withstand the centrifugal forces without increasing the mechanical strength of a chassis of each unit.

Further, the centrifugal forces acting on the units are carried by the mounting members 206b and do not directly act on a fixing means that fixes the units to the mounting members 206b. This construction eliminates a possibility of the fixing means from becoming loose or failing due to excess centrifugal forces or a possibility of the units from coming off.

Further, the mounting members 206b provided to the rotary member 202 are erected almost perpendicular to the mounting surface of the rotary member 202, so that the mounting members 206b increase the section modulus of the rotary member 202, improving the mechanical strength and rigidity without having to increase the plate thickness of the rotary member 202. Because an increase in the mass can be minimized compared with a case where the plate thickness of the rotary member 202 is increased for improved mechanical strength, the moment of inertia can also be reduced.

FIG. 9 and FIG. 10 show a variation of the rotary member 202. Members alike to those of the fourth embodiment carry like reference numbers and their explanations are omitted.

While in the fourth embodiment the rotary member 202 and the unit mounting means 206 are formed integral, this variation adopts an assembly structure.

That is, rectangular accommodating portions 206a are cut away from the unit mounting means 206 of the rotary member 202.

The mounting members 206b for mounting the units have their long side portion 206c and the short side portion 206d separated from each other. The short side portion 206d is formed by bending an edge portion of the accommodating portion 206a almost at right angles to the mounting surface of the rotary member 202. A free end of each short side portion 206d is bent to form a mounting portion 206e.

Both ends of the long side portion 206c of the mounting member 206b are bent to form mounting edges 206f. These mounting edges 206f are secured to the mounting portions 206e of the short side portions 206d by fixing means such as bolts (not shown), thus forming the assembly-structured unit mounting means 206.

The rotary member 202 of the above construction also mounts the units inside the long side portions 206c of the mounting members 206b. As in the preceding embodiments, the centrifugal forces acting on the units when the rotary member 202 is rotated at high speed by the DD motor is carried by the rotary member 202 through the mounting members 206b, thus providing advantages similar to those of the fourth embodiment.

While in the foregoing embodiments, we have described the medical X-ray CT scanner, the present invention can also be applied to industrial X-ray CT scanners, for example, cone beam type X-ray CT scanners using a surface type X-ray detector that combines a scintillator and a photodetector.

What is claimed is:

1. An X-ray CT scanner comprising:

an X-ray radiation means for radiating X-rays against a subject;

an X-ray detection means arranged at a position opposite the X-ray radiation means with respect to the subject;

an opening in which to put the subject;

a rotary member mounting at least the X-ray radiation means and the X-ray detection means and rotated around the subject;

a rotary drive means for rotating the rotary member; and a frame for supporting the rotary member and the rotary drive means;

wherein information on the X-rays that have penetrated the subject and are detected by the X-ray detection means is processed to generate a cross-sectional image of the subject;

wherein the rotary drive means is constructed so that the rotary member is used as a rotor including a rotor core and a plurality of conductors connected to the rotor core with at least one set of stators comprising a stator core and stator winding provided around a part of the rotor and includes a first stator member arranged at an opening side of the rotor and a second stator member disposed at an opposing position via the rotor with respect to the first stator member, and wherein a three-phase AC current is passed through the stator winding to generate a rotating magnetic field between the first and second stator members to rotate the rotor and thereby the rotary member is rotated.

2. The X-ray CT scanner according to claim 1, wherein the rotor includes the rotor core made of a magnetic metal, first and second short-circuit rings and a plurality of conductors connected to the first and second short-circuit rings.

3. The X-ray CT scanner according to claim 2, wherein the rotor core is formed by laminating silicon steel plates punched with a plurality of slots, the conductors are installed in the plurality of slots, and the ends of the conductors are connected to the short-circuit rings.

4. The X-ray CT scanner according to claim 1, wherein when a plurality of stators are provided, they are arranged at almost equal intervals in the circumferential direction of the rotor.

5. An X-ray CT scanner comprising:

an X-ray radiation means for radiating X-rays against a subject;

an X-ray detection means arranged at a position opposite the X-ray radiation means with respect to the subject;

an opening in which to put the subject;

a rotary member mounting at least the X-ray radiation means and the X-ray detection means and rotated around the subject;

a rotary drive means for rotating the rotary member; and a frame for supporting the rotary member and the rotary drive means;

wherein information on the X-rays that have penetrated the subject and are detected by the X-ray detection means is processed to generate a cross-sectional image of the subject;

wherein the rotary drive means is constructed so that the rotary member is used as a rotor includes a magnetic metal body and conductors connected to both surfaces of the magnetic metal body, and at least one set of stators comprising a stator core and stator winding located at opposing positions over both sides of the rotor and includes a first stator member and a second stator member which are arranged at opposing positions via the rotor and wherein a three-phase AC current is passed through the stator winding to generate a rotating magnetic field between the first and second stator members to rotate the rotor and the rotary member is rotated.

6. The X-ray CT scanner according to claim 5, wherein the rotor core is formed by fixing plate conductors to both surfaces of the magnetic metal body.

7. The X-ray CT scanner according to claim 5, wherein when a plurality of stators are provided, they are arranged at almost equal intervals in the circumferential direction of the rotor.

8. An X-ray CT scanner comprising:

an X-ray radiation means for radiating X-rays against a subject;

an X-ray detection means arranged at a position opposite the X-ray radiation means with respect to the subject;

an opening in which the subject is positioned;

a rotary member mounting at least the X-ray radiation means and the X-ray detection means and rotated around the subject;

a rotary drive means for rotating the rotary member; and a frame for supporting the rotary member and the rotary drive means;

wherein information on the X-rays that have penetrated the subject and are detected by the X-ray detection means is processed to generate a cross-sectional image of the subject;

wherein the rotary drive means is constructed so that the rotary member is used as a rotor, and that at least one set of stators is provided around a part of the rotor and comprises a first stator member arranged at an opening side of the rotor and a second stator member arranged at an opposing position via the rotor with respect to the first stator, and wherein a three-phase AC current is passed through the one set of stators to generate a rotating magnetic field between the first and second stator members to rotate the rotor and thereby the rotary member is rotated.

9. An X-ray CT scanner comprising:

an X-ray radiation means for radiating X-rays against a subject;

an X-ray detection means arranged at a position opposite the X-ray radiation means with respect to the subject;

an opening in which the subject is positioned;

a rotary member mounting at least the X-ray radiation means and the X-ray detection means and rotated around the subject;

a rotary drive means for rotating the rotary member; and a frame for supporting the rotary member and the rotary drive means;

wherein information on the X-rays that have penetrated the subject and are detected by the X-ray detection means is processed to generate a cross-sectional image of the subject;

wherein the rotary drive means is constructed so that the rotary member is used as a rotor, and that at least one set of stators is provided so as to sandwich a part of the rotor by an inner circumferential stator and an outer circumferential stator which are arranged in an order of inner circumference stator, rotor and outer circumferential stator from a center of the opening of the rotor in a radial direction; and wherein a three-phase AC current is passed through the one set of stators to generate a rotating magnetic field between the inner circumferential stator and outer circumferential stator to rotate the rotor and thereby the rotary member is rotated.

10. The X-ray CT scanner according to claim 9, wherein the rotor comprises the rotor core made of a magnetic metal, two short-circuit rings provided in a direction of a rotating axis and a plurality of conductors connected to the short-circuit rings.

11. An X-ray CT scanner comprising:

an X-ray radiation means for radiating X-rays against a subject;

an X-ray detection means arranged at a position opposite the X-ray radiation means with respect to the subject;

an opening in which the subject is positioned;

a rotary member mounting at least the X-ray radiation means and the x-ray detection means and rotated around the subject;

a rotary drive means for rotating the rotary member; and a frame for supporting the rotary member and the rotary drive means;

wherein information on the X-rays that have penetrated the subject and are detected by the X-ray detection means is processed to generate a cross-sectional image of the subject;

wherein the rotary drive means is constructed so that the rotary member is used as a rotor, and that at least one set of stators is arranged around a part of the rotor and comprises a first stator member arranged over one side of a rotation plane of the rotor and a second stator member arranged over an other side of the rotation plane, the second stator member being positioned at an opposing position with respect to the first stator member, and wherein a three-phase AC current is passed through the one set of stators to generate a rotating magnetic field between the first and second stator members to rotate the rotor and thereby the rotary member is rotated.

12. The X-ray CT scanner according to claim 11, wherein the rotor comprises a rotor core having two short-circuit rings of different diameter and a plurality of conductors connected to both ends of the short-circuit rings.

13. The X-ray CT scanner according to claim 11, wherein the rotor core is formed with a magnetic metal body and plate conductors connected to both surfaces of the magnetic metal body.

14. An X-ray CT scanner comprising:

an X-ray radiation means for radiating X-rays against a subject;

an X-ray detection means arranged at a position opposite the X-ray radiation means with respect to the subject;

an opening in which the subject is positioned;

a rotary member mounting at least the X-ray radiation means and the X-ray detection means and rotated around the subject;

a rotary drive means for rotating the rotary member; and a frame for supporting the rotary member and the rotary drive means;

wherein information on the X-rays that have penetrated the subject and are detected by the X-ray detection means is processed to generate a cross-sectional image of the subject;

wherein the rotary drive means is constructed so that the rotary member is used as a rotor, and that at least one set of stators including a stator over one side of the rotor and another stator over an other side of the rotor is provided so as to sandwich a part of the rotor in a direction of a rotating axis of the rotor, and wherein, a three-phase AC current is passed through the one set of stators to generate a rotating magnetic field between the first and second stators to rotate the rotor and thereby the rotary member is rotated.

15. The X-ray CT scanner according to claim 14, wherein the rotor comprises a rotor core having two short-circuit rings of different diameter and a plurality of conductors connected to both ends of the short-circuit rings.

* * * * *